(12) United States Patent
Frank et al.

(10) Patent No.: US 7,589,063 B2
(45) Date of Patent: Sep. 15, 2009

(54) MOLECULES WHICH PROMOTE HEMATOPOIESIS

(75) Inventors: Hans-Georg Frank, Kerkrade (NL); Franz-Peter Bracht, Düsseldorf (DE); Udo Haberl, Baesweiler (DE); Andreas Rybka, Herten (DE)

(73) Assignee: Aplagen GmbH, Baesweiler (DE)

( * ) Notice: Subject to any disclaimer, the term of this patent is extended or adjusted under 35 U.S.C. 154(b) by 0 days.

(21) Appl. No.: 11/041,207

(22) Filed: Jan. 25, 2005

(65) Prior Publication Data

US 2006/0128618 A1  Jun. 15, 2006

(30) Foreign Application Priority Data

Dec. 14, 2004  (EP)  ................................... 04029536

(51) Int. Cl.
    *A61K 38/10* (2006.01)
    *A61K 38/08* (2006.01)
    *C07K 7/08* (2006.01)
    *C07K 7/04* (2006.01)

(52) U.S. Cl. ........................... 514/14; 514/15; 530/326; 530/327; 530/328

(58) Field of Classification Search ........................ None
See application file for complete search history.

(56) References Cited

U.S. PATENT DOCUMENTS

| | | | |
|---|---|---|---|
| 4,064,118 A | 12/1977 | Wong | |
| 5,106,954 A | 4/1992 | Fibi et al. | |
| 5,773,569 A | 6/1998 | Wrighton et al. | |
| 6,340,742 B1 | 1/2002 | Burg et al. | |
| 2004/0034888 A1 * | 2/2004 | Liu et al. | 800/289 |
| 2004/0123343 A1 * | 6/2004 | La Rosa et al. | 800/278 |
| 2004/0214272 A1 * | 10/2004 | La Rosa et al. | 435/69.1 |

FOREIGN PATENT DOCUMENTS

| | | |
|---|---|---|
| EP | 1 398 322 A1 | 3/2004 |
| EP | 1 398 327 A1 | 3/2004 |
| EP | 1 398 328 A1 | 3/2004 |
| WO | WO96/40749 | 12/1996 |
| WO | WO 96/40772 | 12/1996 |
| WO | WO 98/25965 | 6/1998 |
| WO | WO 01/38342 A2 | 5/2001 |
| WO | WO01/91780 A1 | 12/2001 |
| WO | WO 03/074567 A2 | 9/2003 |
| WO | WO 2004/002424 A2 | 1/2004 |
| WO | WO 2004/014951 A2 | 2/2004 |
| WO | WO 2004/024761 A2 | 3/2004 |
| WO | WO 2004/100997 A2 | 11/2004 |
| WO | WO 2004/101600 A2 | 11/2004 |
| WO | WO 2004/101606 A2 | 11/2004 |
| WO | WO 2004/101611 A2 | 11/2004 |
| WO | WO 2005/021579 A2 | 3/2005 |
| WO | WO 2006/050959 A2 | 5/2006 |
| WO | WO 2007/101698 A3 | 9/2007 |

OTHER PUBLICATIONS

Ernest H. Rosenbaum, MD, Anemia Causes and Treatment, Cancer Supportive Care Programs, pp. 1-7, Sep. 23, 2003 and updated Sep. 30, 2004, http://www.cancersupportivecare.com/anemiacause.html, printed Sep. 25, 2006.*

Johnson, et al., Identification of a 13 Amino Acid Peptide Mimetic of Erythropoietin and Description of Amino Acids Critical for the Mimetic Activity of EMP1, Biochemistry, 1998, 37, 3699-3710.*

T. Sasaki et al. Nature (2002) 42, pp. 312-316.*

CAS Registry No. 475974-48-2; GenBank 87856, STN entry date Dec. 11, 2002, 1 page.*

Johnson, D.L. et al, "Identification of a 13 amino acid peptide mimetic of erythropoietin and description of amino acids critical for the mimetic activity of EMP1," *Biochemistry*, 37(11):3699-3710 (1998).

Wrighton, N.C. et al., "Increased potency of an erythropoietin peptide mimetic through covalent dimerization," *Nature Biotechnology*, 15:1261-1265 (1997).

Wrighton, N.C. et al., "Small peptide as potent mimetics of the protein hormone erythropoietin," *Science*, 273:458-463 (1996).

U.S. Appl. No. 11/667,290, filed May 9, 2007, Frank et al.

Braisted, A. "Hormone peptidomimetics: seeing double" *Nature Biotechnology;* 15: 1244-1245 (1997).

Cavelier, F., et al. "Original and general strategy of dimerization of bioactive molecules" in "Peptides: The wave of the future" *American Peptide Society:* 152-154 (2001).

Cwirla, S. E., et al. "Peptide agonist of the thrombopoietin receptor as potent as the natural cytokine" *Science;* 276: 1696-1699 (1997).

European Search Report for EP 04 02 9536 dated Feb. 10, 2005.

Haag, R., et al. "An approach to glycerol dendrimers and pseudo-dendritic polyglycerols" *J. Am. Chem. Soc.;* 122: 2954-2955 (2000).

International Search Report for PCT/EP2005/012075 dated Oct. 5, 2006.

Johnson, D. L., et al. "Amino acids critical for the activity of a peptide mimetic of erythropoietin and description of a minimal functional epitope"; 88 (10 Suppl I) AN 2663 p. 661 A; ISSN: 0006-4971 (1996).

Johnson; D. L., et al. "Amino-terminal dimerization of an erythropoietin mimetic peptide results in increased erythropoietic activity" *Chemistry & Biology;* 4(12): 939-950 (1997).

Kuter, D. J., et al. "Recombinant human thrombopoietin: basic biology and evaluation of clinical studies" *Blood;* 100(10): 3457-3469 (2002).

(Continued)

*Primary Examiner*—Andrew D Kosar
(74) *Attorney, Agent, or Firm*—Finnegan, Henderson, Farabow, Garrett & Dunner, LLP

(57) ABSTRACT

Peptides, methods for the preparation thereof, medicaments containing the peptides, and their use in selected indications, such as the treatment of various forms of anemia and stroke.

11 Claims, 2 Drawing Sheets

OTHER PUBLICATIONS

Partial European Search Report for EP 05 01 3594 dated Feb. 24, 2006.
Roberts, M. J., et al. "Chemistry for peptide and protein PEGylation" *Advanced Drug Delivery Reviews:* 54: 459-476 (2002).
Tacey, R., et al. "The detection of anti-erythropoietin antibodies in human serum and plasma Part I. Validation of the protocol for a radioimmunoprecepitation assay" *Journal of Immunological Methods;* 283: 317-329 (2003).
Zalipsky, S., et al. "New detachable poly(ethylene glycol) conjugates: cysteine-cleavable lipopolymers regenerating natural phospholipid, diacyl phosphatidylethanolamine" *Bioconjugate Chemistry;* 10(5): 703-707 (1999).
U.S. Appl. No. 12/281,565, filed Sep. 3, 2008, Frank et al.
International Search Report for PCT Application No. PCT/EP2007/002068 (WO 2007/101698) mailed Oct. 6, 2008.

* cited by examiner

MOLECULES WHICH PROMOTE HEMATOPOIESIS

DESCRIPTION OF THE INVENTION

1. Field of the Invention

The present invention relates to peptides as binding molecules for the erythropoietin receptor, methods for the preparation thereof, medicaments containing these peptides, and their use in selected indications, preferably for treatment of various forms of anemia and stroke.

2. Background of the Invention

The hormone erythropoietin (EPO) is a glycoprotein constituted by 165 amino acids and having four glycosylation sites. The four complex carbohydrate side chains comprise 40 percent of the entire molecular weight of about 35 kD. EPO is formed in the kidneys and from there migrates into the spleen and bone marrow, where it stimulates the production of erythrocytes. In chronic kidney diseases, reduced EPO production results in erythropenic anemia. With recombinant EPO, prepared by genetic engineering, anemias can be treated effectively. EPO improves dialysis patients' quality of life. Not only renal anemia, but also anemia in premature newborns, inflammation and tumor-associated anemias can be improved with recombinant EPO. By means of EPO, a high dosage chemotherapy can be performed more successfully in tumor patients. Similarly, EPO improves the recovery of cancer patients if administered within the scope of radiation therapy.

In the treatment with EPO, there is a problem in that the required dosage regimens are based on frequent or continuous intravenous or subcutaneous applications because the protein is decomposed relatively quickly in the body. Therefore, the evolution of recombinant EPO-derived molecules goes towards selectively modifying the glycoprotein, for example, by additional glycosylation or pegylation, in order to increase stability and thus biological half-life time.

Another important issue associated with the treatment with recombinant EPO is the possibility, that patients develop antibodies to recombinant EPO during treatment. This is due to the fact, that recombinant EPO is not completely identical with endogenous EPO. Once antibody formation is induced, it can lead to antibodies, which compromise the activity of endogenous erythropoietin, too. It frequently increases the dosage of recombinant EPO needed for treatment. Especially if such antibodies compromise the activity of endogenous EPO, this effect can be interpreted as a treatment-induced autoimmune disease. It is especially undesired e.g. in case of dialysis patients undergoing renal transplantation after months or years of EPO-treatment. The antibodies then might compromise the activity of endogenous EPO produced by the transplant and thus compromise erythropoietic activity of the transplanted organ. At the moment, it is an open question, whether the modifications introduced in recombinant EPO in order to increase biological half-life time will aggravate or improve this problem. Generally, it would be expected that extensive modifications and longer half-life time will aggravate this problematic property.

An alternative strategy is the preparation of synthetic peptides from amino acids which do not share sequence homology or structural relationship with erythropoietin. It was shown that peptides, unrelated to the sequence of EPO, which are significantly smaller than erythropoietin can act as agonists (Wrighton et al., 1996). The same authors showed that such peptides can be truncated to still active minimal peptides with length of 10 amino acids.

Synthetic peptides mimeting EPO's activity are subject of the international laid open WO96/40749. It discloses mimetic peptides of 10 to 40 amino acids of a distinct consensus preferably containing two prolines, one of which is considered to be essential.

Such peptides can be produced chemically and do not need recombinant production, which is much more difficult to control and to yield products with defined quality and identity. Chemical production of peptides of such a small size can also be competitive in terms of production costs. Moreover, chemical production allows defined introduction of molecular variations such as glycosylation, pegylation or any other defined modifications, which might have a known potency to increase biological half-life. However, so far there has been no approval of any therapy with EPO mimetic peptides.

Thus it is the objective of the present invention to provide alternative synthetic peptides which exhibit at least essential parts of the biological activity of the native EPO and thus provide alternative means for efficient therapeutic strategies, in particular for the treatment of anemia or stroke.

SUMMARY OF THE INVENTION

According to the invention there is provided a synthetic peptide that binds to the erythropoietin receptor and comprises a sequence of amino acids $CX_3X_4Z_1Z_2X_5TWX_6C$ (SEQ ID No:1), wherein each of the amino acid is indicated by standard letter abbreviation and $X_3$ is R,H,L, or W, $X_4$ is M,F, or I, $X_5$ is independently selected from any amino acids, $X_6$ is D,E,I,L, or V, $Z_1$ is G or a conservative exchange of G and $Z_2$ is a non-conservative exchange of P. The length of the peptide is preferably between 10 to forty amino acids.

To date, all small peptide-based agonists of the EPO receptor have had a structure which contains at least one proline, often two proline residues in defined positions, usually numbered as position 10 and 17, referenced to their position in the very active erythropoietin-mimetic peptide EMP1 (international laid pen WO/96/40749). These prolines are considered indispensable to the effectiveness of the peptides. In the case of the proline at position 17, this has been substantiated by interactions with the receptor, while the proline at position 10 was thought to be necessary for the correct folding of the molecule (see also Wrighton et al. 1996, 1997). The correct folding, supported by the specific stereochemical properties of proline, is usually a necessary precondition of biological activity. Generally, proline is a structure-forming amino acid which is often involved—as in this case—in the formation of hairpin structures and beta turns. Due to this property, inter alia, it is a frequent point of attack for post-proline-specific endopeptidases which destroy proline-containing peptides/proteins. A number of endogenous peptide hormones (angiotensins I and II, urotensins, thyreoliberin, other liberins, etc.) are inactivated by such "single-hit" post-proline cleavage. Half-life time of proline-containing EPO-mimetic peptides is thus shortened by the activity of these frequent and active enzymes.

Thus, it was very surprising, that the peptides according to the invention do exhibit mimetic activities although both prolines may be replaced by other natural or non-natural amino acids. In fact the peptides according to the invention have an activity comparable to that of proline-containing peptides. However, it is noteworthy that the amino acids substituting proline residues do not represent a conservative exchange. Moreover, the sequences can have N-terminal and/or C-terminal acetylation and amidation.

DESCRIPTION OF THE EMBODIMENTS

Figure 1:
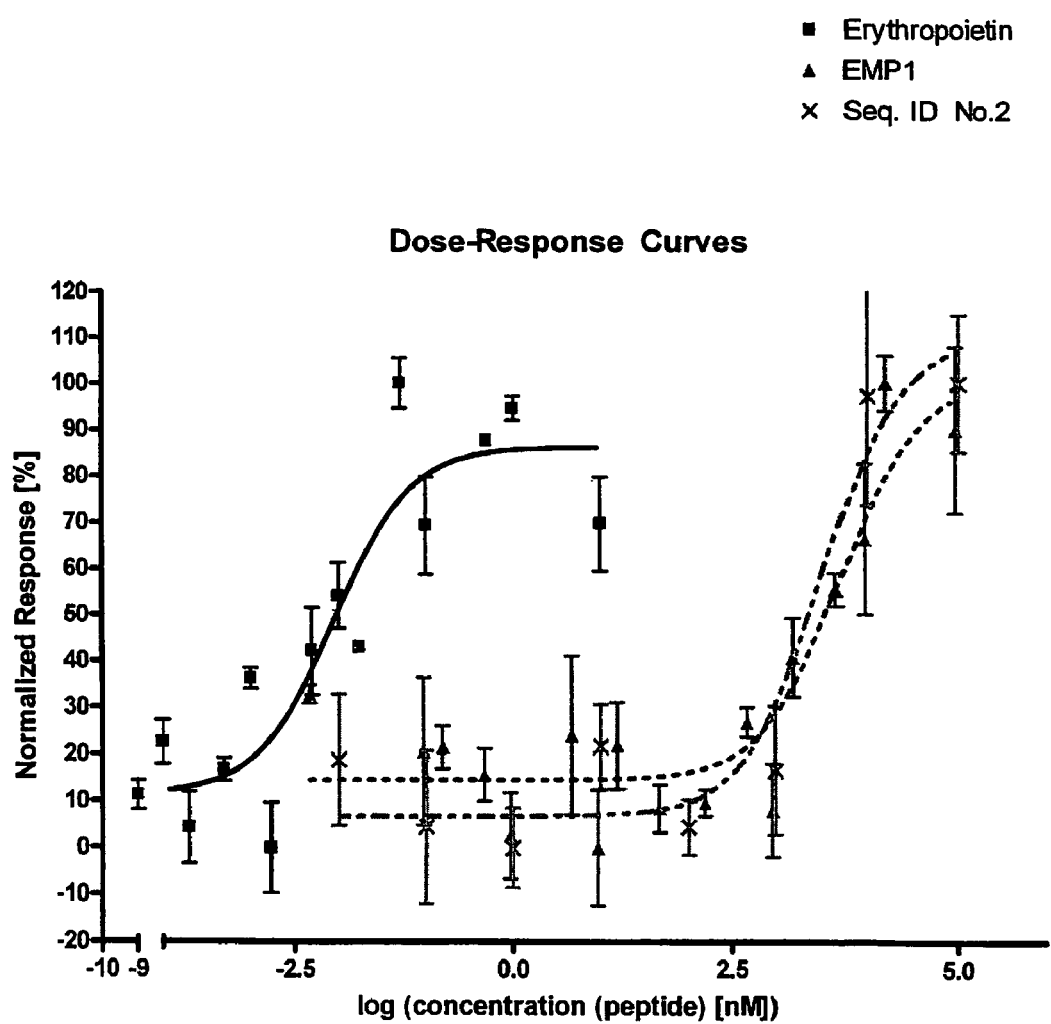
FIGS. 1 and 2 show dose response curves of erythropoietin mimetic peptides determined from raw data obtained by assays described in example 3b and curves fitted with the program GraphPad Prism version 4.

In one preferred embodiment of the invention the peptides do have a single amino acid substituting the amino acid residues $Z_1$ and $Z_2$. Preferably both residues are substituted by one non-natural amino acid, e.g. 5-aminolevulinic acid or aminovaleric acid.

In a further embodiment, the peptides according to the invention comprise $X_2$ in a sequence of amino acids $YX_2CX_3X_4Z_1Z_2X_5TWX_6C$ (SEQ ID No:3), wherein $X_2$ is independently selected from any of the amino acids.

The peptide according to the invention may be extended and may comprises the consensus sequence $X_1YX_2CX_3X_4Z_1Z_2X_5TWX_6CX_7X_8X_9$ (SEQ ID No:9), wherein $X_1, X_7$, and $X_9$ are independently selected from any amino acids and $X_8$ is an amino acid with A,G,P,R,K, or a non-natural amino acid with positively charged side chain.

In a further embodiment of the invention it is preferred that peptides comprise $X_3$ as R or H and/or $X_4$ as F or M and/or $X_5$ as I,L,T,M or V and/or $X_6$ as D or V and/or $X_7$ as G,K,L,Q,R,S or T and/or $X_8$ as R,K or a non-natural amino acid with positively charged side chain.

The peptides according to the invention may comprise $X_1$ as D,E,L,N,S,T or V and/or $X_2$ as A,H,K,L,M,S or T and/or $X_7$ is K,R,S or T and/or $X_8$ is K or a non-natural amino acid with positively charged side chain.

At the beginning (N terminal) and end (C terminal) of the individual peptide sequences, up to five amino acids may be removed and/or added. In the present invention, the abbreviations for the one-letter code as capital letters are those of the standard polypeptide nomenclature, extended by the addition of non-natural amino acids.

| Code | Amino acid |
|---|---|
| A | L-alanine |
| V | L-valine |
| L | L-leucine |
| I | L-isoleucine |
| M | L-methionine |
| F | L-phenylalanine |
| Y | L-tyrosine |
| W | L-tryptophan |
| H | L-histidine |
| S | L-serine |
| T | L-threonine |
| C | L-cysteine |
| N | L-asparagine |
| Q | L-glutamine |
| D | L-aspartic acid |
| E | L-glutamic acid |
| K | L-lysine |
| R | L-arginine |
| P | L-proline |
| G | glycine |
| Ava, 5-Ava | 5-aminovaleric acid |
| Als, 5-Als | 5-aminolevulinic acid |

The present invention includes modifications of the peptides by conservative exchanges of single amino acids. Such an exchange alters the structure and function of a binding molecule but slightly in most cases. In a conservative exchange, one amino acid is replaced by another amino acid within a group with similar properties.

Examples of corresponding groups are:
amino acids having non-polar side chains: A, G, V, L, I, P, F, W, M
uncharged amino acids having polar side chains: S, T, G, C, Y, N, Q
amino acids having aromatic side chains: F, Y, W
positively charged amino acids: K, R, H
negatively charged amino acids: D, E
amino acids of similar size or molecular weight, wherein the molecular weight of the replacing amino acids deviates by a maximum of +/−25% from the molecular weight of the original amino acid.

More specifically, Wrighton et al. (U.S. Pat. No. 5,773,569, and associated patents) examined in detail, using phage display techniques, which amino acids can be replaced, while maintaining the activity. They also investigated and published data on possible truncation, i.e. minimal length of a given peptide. However, under the conditions of phage display, a proline near the central Gly-residue seemed to be the only possibility to obtain active peptides.

In a further preferred embodiment of the invention there are provided peptides selected from the group consisting of SEQ ID NOS. 2,4-8 given below:

```
SEQ. ID NO. 2:    GGTYSCHFGKLTWVCKKQGG
SEQ. ID NO. 4:    GGTYSCHFGKLTWVCKPQGG
SEQ. ID NO. 5:    GGTYSCHFGRLTWVCKPQGG
SEQ. ID NO. 6:    GGTYSCHFGRLTWVCKKQGG
```

Incorporation of 5-aminolevulinic acid (Als):

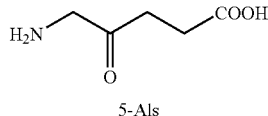

5-Als

```
SEQ. ID NO. 7:    GGTYSCHF-(Als)-LTWVCKPQGG
SEQ. ID NO. 8:    GGTYSCHF-(Als)-LTWVCKKQGG
```

The peptides according to the invention may be included into a pharmaceutical composition, which may further comprise pharmaceutical carrier(s). The composition may contain one or two peptides. This composition may b used for the treatment for e.g. of type of anemia and stroke.

EXAMPLES

Example 1

An example of the synthesis of peptides of this invention is the following procedure:

Example 1a

Manual Synthesis

The synthesis is carried out by the use of a Discover microwave system (CEM) using PL-Rink-Amide-Resin (subtitution rate 0.4 mmol/g) or preloaded Wang-Resins in a scale of 0.4 mmol. Removal of Fmoc-group is achieved by addition of 30 ml piperidine/DMF (1:3) and irradiation with 100 W for 3×30 sec. Coupling of amino acids is achieved by addition of 5 fold excess of amino acid in DMF PyBOP/HOBT/DIPEA as coupling additives and irradiation with 50 W for 5×30 sec. Between all irradiation cycles the solution is cooled manually with the help of an ice bath. After deprotection and coupling, the resin is washed 6 times with 30 ml DMF. After deprotection of the last amino acid some peptides are acetylated by incubation with 1.268 ml of capping solution (4.73 ml acetic anhydride and 8.73 ml DIEA in 100 ml DMSO) for 5 minutes. Before cleavage, the resin is then washed 6 times with 30 ml DMF and 6 times with 30 ml DCM. Cleavage of the crude peptides is achieved by treatment with 5 ml TFA/TIS/EDT/$H_2O$ (94/1/2.5/2.5) for 120 minutes under inert atmosphere. This solution is filtered into 40 ml cold ether. The precipitate is dissolved in acetonitrile/water (1/1) and the peptide is purified by RP-HPLC (Kromasil 100 C18 10 μm, 250×4.6 mm).

Example 1b

Automated Synthesis

The synthesis is carried out by the use of an Odyssey microwave system (CEM) using PL-Rink-Amide-Resins (substitution rate 0.4 mmol/g) or preloaded Wang-Resins in a scale of 0.25 mmol. Removal of Fmoc-groups is achieved by addition of 10 ml piperidine/DMF (1:3) and irradiation with 100 W for 10×10 sec. Coupling of amino acids is achieved by addition of 5 fold excess of amino acid in DMF PyBOP/HOBT/DIPEA as coupling additives and irradiation with 50 W for 5×30 sec. Between all irradiation cycles the solution is cooled by bubbling nitrogen through the reaction mixture. After deprotection and coupling, the resin is washed 6 times with 10 ml DMF. After deprotection of the last amino acid, some peptides are acetylated by incubation with 0.793 ml of capping-solution (4.73 ml acetic anhydride and 8.73 ml DIEA in 100 ml DMSO) for 5 minutes. Before cleavage the resin is then washed 6 times with 10 ml DMF and 6 times with 10 ml DCM. Cleavage of the crude peptides is achieved by treatment with 5 ml TFA/TIS/EDT/$H_2O$ (94/1/2.5/2.5) for 120 minutes under an inert atmosphere. This solution is filtered into 40 ml cold ether, the precipitate dissolved in acetonitrile/water (1/1) and the peptide is purified by RP-HPLC (Kromasil 100 C18 10 μm, 250×4.6 mm).

Purification

All peptides were purified using a Nebula-LCMS-system (Gilson). The crude material of all peptides was dissolved in acetonitrile/water (1/1) and the peptide purified by RP-HPLC (Kromasil 100 C18 10 μm, 250×4.6 mm). The flow rate was 20 ml/min and the LCMS split ratio 1/1000.

Example 2

Formation of the Intramolecular Disulfide Bridges

Example 2a

Cyclization with $K_3[(FeCN_6)]$

Solution1: 10 mg of the peptide are dissolved in 0.1% TFA/acetonitrile and diluted with water until a concentration of 0.5 mg/ml is reached. Solid ammonium bicarbonate is added to reach a pH of app. 8.

Solution 2: In a second vial 10 ml 0.1% TFA/acetonitrile are diluted with 10 ml of water. Solid ammoniumbicarbonate is added until a pH of 8 is reached and 1 drop of a 0.1M solution of $K_3[(FeCN_6)]$ is added.

Solution 1 and 2 are added dropwise over a period of 3 hours to a mixture of acetonitrile/water (1/1; pH=8). The mixture is incubated at room temperature overnight and the mixture concentrated and purified by LCMS.

Example 2b

Cyclization with CLEAR-OX™-Resin

To 100 ml of acetonitrile/water (1/1; 0.1% TFA), solid ammonium bicarbonate is added until a pH of 8 is reached. This solution is degassed by bubbling Argon for 30 minutes. Now 100 mg of CLEAR-OX™-resin is added. After 10 minutes, 10 mg of the peptide is added as a solid. After 2 h of incubation, the solution is filtered, concentrated and purified by LCMS.

Purification of Cyclic Peptides:

All peptides were purified using a Nebula-LCMS-system (Gilson). The crude material of all peptides was dissolved in acetonitrile/water (1/1) or DMSO and the peptide was purified by RP-HPLC (Kromasil 100 C18 or C8 10 μm, 250×4.6 mm). The flow rate was 20 ml/min and the LCMS split ratio 1/1000.

Example 3

In-Vitro Assays

Example 3a

Proliferation Assay with TF-1 Cells by BrdU Incorporation

TF-1 Cells in logarithmic growth phase (~$2\times10^5$–$1\times10^6$ cells/ml; RPMI medium; 20% fetal calf serum; supplemented with Penicillin, streptomycin, L-Glutamine; 0.5 ng/ml Interleukin 3) are washed (centrifuge 5 min. 1500 rpm and resuspend in RPMI complete without IL3 at 500,000 cells/ml) and precultured before start of the assay for 24 h without IL-3. At the next day the cells are seeded in 24- or 96-well plates usually using at least 6 concentrations and 4 wells per concentration containing at least 10,000 cells/well per agent to be tested. Each experiment includes controls comprising recombinant EPO as a positive control agent and wells without addition of cytokine as negative control agent. Peptides and EPO-controls are prediluted in medium to the desired concentrations and added to the cells, starting a culture period of 3 days under standard culture conditions (37° C., 5% carbon dioxide in the gas phase, atmosphere saturated with water). Concentrations always refer to the final concentration of agent in the well during this 3-day culture period. At the end of this culture period, FdU is added to a final concentration of 8 ng/ml culture medium and and the culture continued for 6 hours. Then, BrdU (bromodeoxyuridine) and dCd (2-deoxycytidine) are added to their final concentrations (10 ng/ml BrdU; 8 ng/ml dCD; final concentrations in culture medium) and culture continued for additional 2 hours.

At the end of this incubation and culture period, the cells are washed once in phosphate buffered saline containing 1.5% BSA and resuspended in a minimal amount liquid. From this suspension, cells are added dropwise into 70% ethanol at −20° C. From here, cells are either incubated for 10 min. on ice and then analysed directly or can be stored at 4° C. prior to analysis.

Prior to analysis, cells are pelleted by centrifugation, the supernatant is discarded and the cells resuspended in a minimal amount of remaining fluid. The cells are then suspended and incubated for 10 min. in 0.5 ml 2M HCl/0.5% triton X-100. Then, they are pelleted again and resuspended in a minimal amount of remaining fluid, which is diluted with 0.5 ml of 0.1 N $Na_2B_4O_7$, pH 8.5 prior to immediate repelleting of the cells. Finally, the cells are resuspended in 40 µl of phosphate buffered saline (1.5% BSA) and divided into two reaction tubes containing 20 µl cell suspension each. 2 µl of anti-BrdU-FITC (DAKO, clone Bu20a) are added to one tube and 2 µl control mIgG1-FITC (Sigma) are added to the second tube starting an incubation period of 30 min. at room temperature. Then, 0.4 ml of phosphate buffered saline and 10 µg/ml Propidium Iodide (final concentration) are added. Analysis in the flow cytometer refers to the fraction of 4C cells or cells with higher ploidy and to the fraction of BrdU-positive cells, thus determining the fraction of cells in the relevant stages of the cell cycle.

Example 3b

Proliferation Assay with TF-1 Cells by MTT

TF-1 Cells in logarithmic growth phase (~$2 \times 10^5$–$1 \times 10^6$ cells/ml; RPMI medium; 20% fetal calf serum; supplemented with Penicillin, streptomycin, L-Glutamine; 0.5 ng/ml Interleukin 3) are washed (centrifuge 5 min. 1500 rpm and resuspend in RPMI complete without IL3 at 500,000 cells/ml) and pre-cultured before start of the assay for 24 h without IL-3. At the next day the cells are seeded in 24- or 96-well plates usually using at least 6 concentrations and 4 wells per concentration containing at least 10,000 cells/well per agent to be tested. Each experiment includes controls comprising recombinant EPO as a positive control agent and wells without addition of cytokine as negative control agent. Peptides and EPO-controls are prediluted in medium to the desired concentrations and added to the cells, starting a culture period of 3 days under standard culture conditions (37° C., 5% carbon dioxide in the gas phase, atmosphere saturated with water). Concentrations always refer to the final concentration of agent in the well during this 4-day culture period.

At day 4, prior to start of the analysis, a dilution series of a known number of TF-1 cells is prepared in a number of wells (0/2500/5000/10000/20000/50000 cells/well in 100 µl medium). These wells are treated in the same way as the test wells and later provide a calibration curve from which cell numbers can be determined. Having set up these reference wells, MTS and PMS from the MTT proliferation kit (Promega, CellTiter 96 Aqueous non-radioactive cell proliferation assay) are thawed in a 37° C. waterbath and 100 µl of PMS solution are added to 2 ml of MTS solution. 20 µl of this mixture are added to each well of the assay plates and incubated at 37° C. for 3-4 h. 25 µl of 10% sodium dodecylsulfate in water are added to each well prior to measurement E492 in an ELISA Reader.

Figure 2:
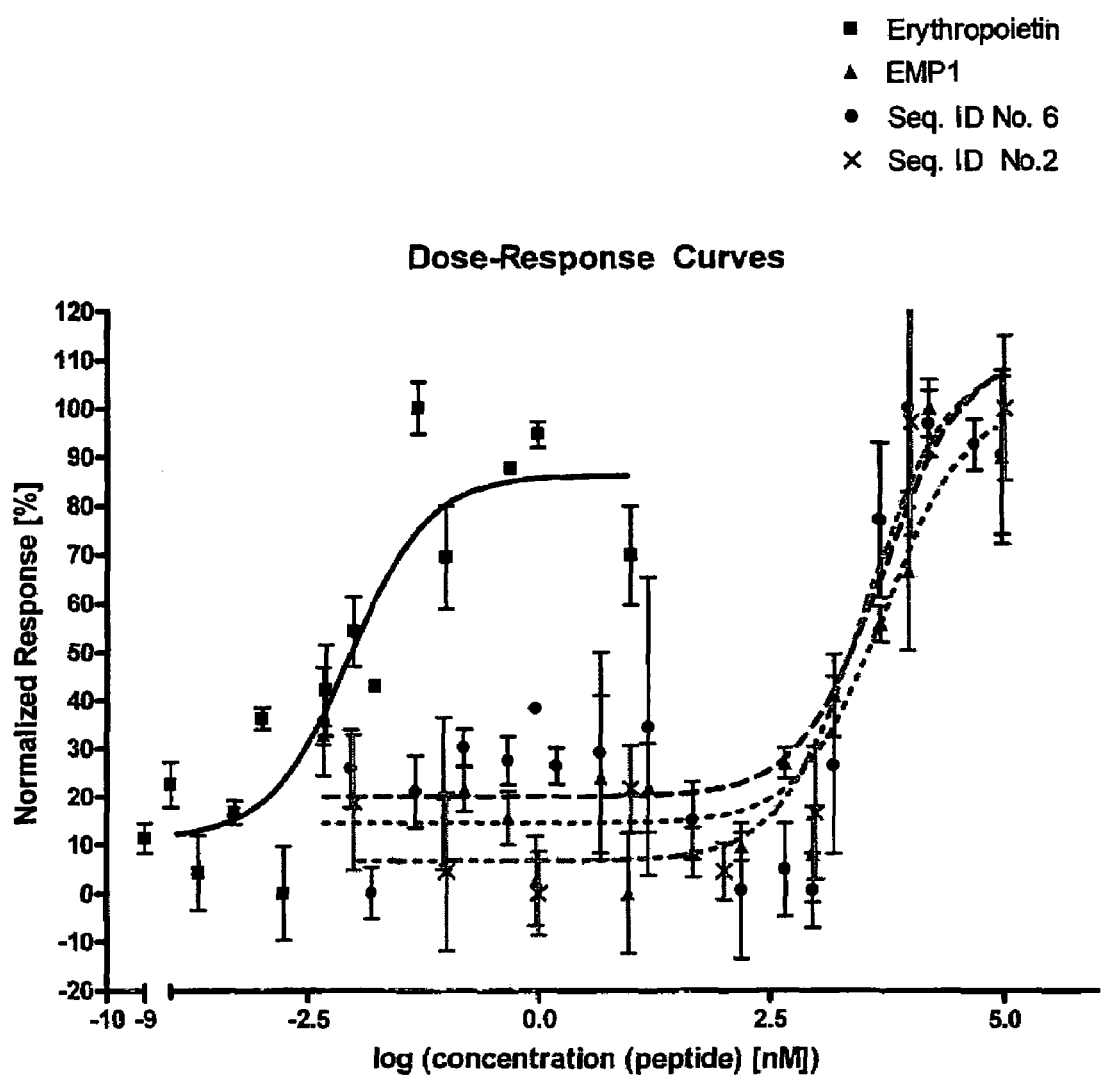

Using graphical evaluations as shown in FIGS. 1 and 2 based on calculations of the dose-response relationship using the program GraphPad the following $EC_{50}$ values were determined on the basis of MTT-assay data:

The following table shows the $EC_{50}$ values of some exemplary peptides:

| | | |
|---|---|---|
| SEQ. ID NO. 2: | GGTYSCHFGKLTWVCKKQGG | 3284 nmol/l |
| SEQ. ID NO. 4: | GGTYSCHFGKLTWVCKPQGG | 4657 nmol/l |
| SEQ. ID NO. 5: | GGTYSCHFGRLTWVCKPQGG | 5158 nmol/l |
| SEQ. ID NO. 6: | GGTYSCHFGRLTWVCKKQGG | 4969 nmol/l |
| SEQ. ID NO. 7: | GGTYSCHF-(Als)-LTWVCKPQGG | 5264 nmol/l |
| SEQ. ID NO. 8: | GGTYSCHF-(Als)-LTWVCKKQGG | 4996 nmol/l |
| SEQ. ID NO. 10: | GGTYSCHFGPLTWVCKKQGG | 2518 nmol/l |
| SEQ. ID NO. 11: | GGTYSCHFAKLTWVCKKQGG | 5045 nmol/l |
| SEQ. ID NO. 12: | GGTYSCHFGGLTWVCKPQGG | no activity detectable |

REFERENCES

Wrighton N C, Balasubramanian P, Barbone F P, Kashyap A K, Farrell F X, Jolliffe L, Barrett R W, Dower W J (1997) Increased potency of an erythropoietin peptide mimetic through covalend dimerization. Nature Biotechnology 15:1261-1265

Wrighton N C, Farrell F X, Chang R, Kashyap A K, Barbone F P, Mulcahy L S, Johnson D L, Barrett R W, Jolliffe L K, Dower W J (1996) Small Peptides as Potent Mimetics of the Protein Hormone Erythropoietin. Science 273:458-463

---

What is claimed is:

1. A peptide comprising the sequence $CX_3X_4Z_1Z_2X_5TWX_6C$ (SEQ ID NO:1), wherein:
   $X_3$ is R, H, L or W;
   $X_4$ is M,F, or I;
   $X_5$ is any amino acid;
   $X_6$ is D, E, I, L or V;
   $Z_1$ is G, A, V, L, I, P, F, W or M; and
   $Z_2$ is S, T, C, Y, N, Q, F, W, K, R, H, D, E, 5-aminovaleric acid (Ava) or 5-aminolevulinic acid (Als) or an amino acid with a positively charged side chain;
   wherein the peptide binds to the erythropoietin receptor.

2. The peptide of claim 1, wherein $Z_2$ is an amino acid with a positively charged side chain.

3. The peptide of claim 2, wherein $Z_2$ is R, K or a non-natural amino acid with a positively charged side chain.

4. The peptide of claim 1, wherein the peptide comprises the sequence $YX_2CX_3X_4Z_1Z_2X_5TWX_6C$ (SEQ ID NO:3), wherein:
   $X_2$ is any amino acid.

5. The peptide of claim 1, wherein the peptide comprises the sequence $X_1YX_2CX_3X_4Z_1Z_2X_5TWX_6CX_7X_8X_9$ (SEQ ID NO :9), wherein:
   $X_1, X_2, X_7$ and $X_9$ are any amino acid; and
   $X_8$ is A, G, P, R, K or a non-natural amino acid with a positively charged side chain.

6. The peptide of claim 5, wherein one or more of (a)-(f) applies:
   (a) $X_3$ is R or H;
   (b) $X_4$ is F or M;
   (c) $X_5$ is I, L, T, M or V;
   (d) $X_6$ is D or V;
   (e) $X_7$ is G, K, L, Q, R, S or T; and
   (f) $X_8$ is R, K or a non-natural amino acid with a positively charged side chain.

7. The peptide of claim 5, wherein one or more of (g)-(k) applies:
   (g) $X_1$ is D, E, L, N, S, T or V;
   (h) $X_2$ is A, H, K, L, M, S or T;
   (i) $X_7$ is K, R, S or T;
   (j) $X_8$ is K or a non-natural amino acid with a positively charged side chain; and
   (k) $Z_1$ is G.

8. A peptide comprising SEQ ID NO:2, 4, 5 or 6, wherein said peptide binds to the erythropoietin receptor.

9. A composition comprising at least one peptide of claim 1, in combination with at least one pharmaceutically acceptable carrier.

10. A method of treating anemia or stroke, comprising administering to a patient in need thereof, an effective amount of at least one peptide of claim 1.

11. A method of treating anemia or stroke, comprising administering to a patient in need thereof, an effective amount of the composition of claim 9.

* * * * *

UNITED STATES PATENT AND TRADEMARK OFFICE
CERTIFICATE OF CORRECTION

| | | |
|---|---|---|
| PATENT NO. | : 7,589,063 B2 | Page 1 of 1 |
| APPLICATION NO. | : 11/041207 | |
| DATED | : September 15, 2009 | |
| INVENTOR(S) | : Frank et al. | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 0 days.

Delete the phrase "by 0 days" and insert -- by 269 days --

Signed and Sealed this

Fourth Day of May, 2010

David J. Kappos
*Director of the United States Patent and Trademark Office*

SEQUENCE LISTING

<160> NUMBER OF SEQ ID NOS: 12

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic Peptide
<220> FEATURE:
<221> NAME/KEY: MOD_RES
<222> LOCATION: (2)
<223> OTHER INFORMATION: R, H L or W
<220> FEATURE:
<221> NAME/KEY: MOD_RES
<222> LOCATION: (3)
<223> OTHER INFORMATION: M, F or I
<220> FEATURE:
<221> NAME/KEY: MOD_RES
<222> LOCATION: (4)
<223> OTHER INFORMATION: G or a conservative exchange of G
<220> FEATURE:
<221> NAME/KEY: MOD_RES
<222> LOCATION: (5)
<223> OTHER INFORMATION: a non-conservative exchange of P
<220> FEATURE:
<221> NAME/KEY: MOD_RES
<222> LOCATION: (6)
<223> OTHER INFORMATION: any amino acid
<220> FEATURE:
<221> NAME/KEY: MOD_RES
<222> LOCATION: (9)
<223> OTHER INFORMATION: D, E, I, L or V

<400> SEQUENCE: 1

Cys Xaa Xaa Xaa Xaa Xaa Thr Trp Xaa Cys
 1               5                  10

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 2

Gly Gly Thr Tyr Ser Cys His Phe Gly Lys Leu Thr Trp Val Cys Lys
 1               5                  10                  15

Lys Gln Gly Gly
            20

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic Peptide
<220> FEATURE:
<221> NAME/KEY: MOD_RES

```
<222> LOCATION: (2)
<223> OTHER INFORMATION: any amino acid
<220> FEATURE:
<221> NAME/KEY: MOD_RES
<222> LOCATION: (4)
<223> OTHER INFORMATION: R, H L or W
<220> FEATURE:
<221> NAME/KEY: MOD_RES
<222> LOCATION: (5)
<223> OTHER INFORMATION: M, F or I
<220> FEATURE:
<221> NAME/KEY: MOD_RES
<222> LOCATION: (6)
<223> OTHER INFORMATION: G or a conservative exchange of G
<220> FEATURE:
<221> NAME/KEY: MOD_RES
<222> LOCATION: (7)
<223> OTHER INFORMATION: a non-conservative exchange of P
<220> FEATURE:
<221> NAME/KEY: MOD_RES
<222> LOCATION: (8)
<223> OTHER INFORMATION: any amino acid
<220> FEATURE:
<221> NAME/KEY: MOD_RES
<222> LOCATION: (11)
<223> OTHER INFORMATION: D, E, I L or V

<400> SEQUENCE: 3

Tyr Xaa Cys Xaa Xaa Xaa Xaa Xaa Thr Trp Xaa Cys
 1               5                  10

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

Gly Gly Thr Tyr Ser Cys His Phe Gly Lys Leu Thr Trp Val Cys Lys
 1               5                  10                  15

Pro Gln Gly Gly
            20

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Gly Gly Thr Tyr Ser Cys His Phe Gly Arg Leu Thr Trp Val Cys Lys
 1               5                  10                  15

Pro Gln Gly Gly
            20

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Gly Gly Thr Tyr Ser Cys His Phe Gly Arg Leu Thr Trp Val Cys Lys
 1               5                  10                  15
```

Lys Gln Gly Gly
            20

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (9)
<223> OTHER INFORMATION: 5-aminolevulinic acid (ALS)

<400> SEQUENCE: 7

Gly Gly Thr Tyr Ser Cys His Phe Xaa Leu Thr Trp Val Cys Lys Pro
 1               5                  10                  15

Gln Gly Gly

<210> SEQ ID NO 8
<211> LENGTH: 19
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (9)
<223> OTHER INFORMATION: 5-aminolevulinic acid (ALS)

<400> SEQUENCE: 8

Gly Gly Thr Tyr Ser Cys His Phe Xaa Leu Thr Trp Val Cys Lys Lys
 1               5                  10                  15

Gln Gly Gly

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (1)
<223> OTHER INFORMATION: any amino acid
<220> FEATURE:
<221> NAME/KEY: MOD_RES
<222> LOCATION: (3)
<223> OTHER INFORMATION: any amino acid
<220> FEATURE:
<221> NAME/KEY: MOD_RES
<222> LOCATION: (5)
<223> OTHER INFORMATION: R, H L or W
<220> FEATURE:
<221> NAME/KEY: MOD_RES
<222> LOCATION: (6)
<223> OTHER INFORMATION: M, F or I
<220> FEATURE:
<221> NAME/KEY: MOD_RES
<222> LOCATION: (7)
<223> OTHER INFORMATION: G or a conservative exchange of G
<220> FEATURE:
<221> NAME/KEY: MOD_RES
<222> LOCATION: (8)
<223> OTHER INFORMATION: a non-conservative exchange of P
<220> FEATURE:
<221> NAME/KEY: MOD_RES
<222> LOCATION: (9)

```
<223> OTHER INFORMATION: any amino acid
<220> FEATURE:
<221> NAME/KEY: MOD_RES
<222> LOCATION: (12)
<223> OTHER INFORMATION: D, E, I L or V
<220> FEATURE:
<221> NAME/KEY: MOD_RES
<222> LOCATION: (14)
<223> OTHER INFORMATION: any amino acid
<220> FEATURE:
<221> NAME/KEY: MOD_RES
<222> LOCATION: (15)
<223> OTHER INFORMATION: A, G, P, R, K or a non-natural amino acid with
      a positively charged side chain
<220> FEATURE:
<221> NAME/KEY: MOD_RES
<222> LOCATION: (16)
<223> OTHER INFORMATION: any amino acid

<400> SEQUENCE: 9

Xaa Tyr Xaa Cys Xaa Xaa Xaa Xaa Xaa Thr Trp Xaa Cys Xaa Xaa Xaa
 1               5                  10                  15

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 10

Gly Gly Thr Tyr Ser Cys His Phe Gly Pro Leu Thr Trp Val Cys Lys
 1               5                  10                  15

Lys Gln Gly Gly
            20

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 11

Gly Gly Thr Tyr Ser Cys His Phe Ala Lys Leu Thr Trp Val Cys Lys
 1               5                  10                  15

Lys Gln Gly Gly
            20

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 12

Gly Gly Thr Tyr Ser Cys His Phe Gly Gly Leu Thr Trp Val Cys Lys
 1               5                  10                  15

Pro Gln Gly Gly
            20
```